US00RE40901E

(19) United States
(12) Reissued Patent
Bombardelli et al.

(10) Patent Number: US RE40,901 E
(45) Date of Reissued Patent: Sep. 1, 2009

(54) TAXANE DERIVATIVES AND PROCESSES FOR THE PREPARATION THEREOF

(75) Inventors: Ezio Bombardelli, Groppello Cairoli (IT); Bruno Gabetta, Milan (IT); Alessandro Pontiroli, Milan (IT)

(73) Assignee: Indena S.p.A., Milan (IT)

(21) Appl. No.: 11/820,012

(22) PCT Filed: Jul. 3, 2000

(86) PCT No.: PCT/EP00/06185

§ 371 (c)(1),
(2), (4) Date: Apr. 23, 2002

(87) PCT Pub. No.: WO01/02407

PCT Pub. Date: Jan. 11, 2001

Related U.S. Patent Documents

Reissue of:
(64) Patent No.: 6,906,101
Issued: Jun. 14, 2005
Appl. No.: 10/019,252
Filed: Apr. 23, 2002

(30) Foreign Application Priority Data

Jul. 6, 1999 (IT) ..... MI99A001483

(51) Int. Cl.
*A61K 31/335* (2006.01)
*C07D 317/70* (2006.01)

(52) U.S. Cl. ..... 514/463; 549/432
(58) Field of Classification Search ..... 514/463; 569/432
See application file for complete search history.

(56) References Cited

U.S. PATENT DOCUMENTS

| | | | |
|---|---|---|---|
| 5,476,954 | A | 12/1995 | Bourzat et al. |
| 5,621,121 | A | 4/1997 | Commercon et al. |
| 5,705,508 | A | 1/1998 | Ojima et al. |
| 5,750,562 | A | 5/1998 | Bombardelli et al. |
| 5,763,628 | A | 6/1998 | Bourzat et al. |

OTHER PUBLICATIONS

Bristol–Myers Squibb Patient Information for Taxol, Mar. 2003.* www.cancer.gov/cancertopics/alphalist accessed Jul. 15, 2008.*

Appendino et al., "Synthesis and Evaluation of C–Seco–Paclitaxel Analogues", *Tetrahedron Letters,* vol. 38: No. 24 pp. 4273–4276 (1997).

Ojima et al., "Synthesis and Structure–Activity Relationships of Taxoids Derived From 14β–Hydroxy–10–deacetylbaccatin III", *J. Med. Chem.* vol. 40: No. 2, pp. 267–278 (1997).

* cited by examiner

*Primary Examiner*—Rei-Tsang Shiao
*Assistant Examiner*—Joseph R Kosack
(74) *Attorney, Agent, or Firm*—Jones Day

(57) ABSTRACT

A novel taxane derivative with anticancer activity, a process for its preparation and a process for the preparation of 14-β-hydroxy-1,14-carbonate-baccatine III and V derivatives 13-substituted by an isoserine residue.

34 Claims, No Drawings

TAXANE DERIVATIVES AND PROCESSES FOR THE PREPARATION THEREOF

Matter enclosed in heavy brackets [ ] appears in the original patent but forms no part of this reissue specification; matter printed in italics indicates the additions made by reissue.

TECHNICAL FIELD

The present invention relates to a novel taxane useful as chemotherapeutic agent, the pharmaceutical compositions containing it and a process for the preparation of 14-β-hydroxy-1,14-carbonate-baccatine III and V derivatives, substituted at the 13 position by an isoserine residue.

BACKGROUND OF THE INVENTION

Taxanes are one of the most important classes of anticancer drugs recently developed. The remarkable effectiveness of Paclitaxel and of its analogue Docetaxel in the treatment of several tumors has focused research on substances with antimicrotubular activity. Taxanes are however characterized by a particular action mechanism, in that they promote the assembly of microtubules and inhibit tubuline depolymerization.

The main drawbacks of the taxanes presently used are: (a) insolubility in water, making mandatory the use of specific carriers which can cause hypersensitization reactions, (b) toxicities which limit dosages, (c) development of resistance mechanisms. Cell resistance to taxanes has been related to the MDR phenotype ("multidrug resistance") mediated by the P-glycoprotein transporter, by tubuline alterations, and by changes in the expression of apoptotic regulatory proteins.

In order to find novel active molecules having higher solubility and better tolerability, 14β-hydroxy-10-deacetylbaccatine III and V taxane derivatives have been synthesized.

Some derivatives of 14-hydroxy baccatine III substituted at the 13-position by isoserine residues are disclosed in U.S. Pat. No. 5,705,508, together with a process for the preparation thereof.

SUMMARY OF THE INVENTION

It has now been found that the compound of formula (I), a 14β-hydroxy-1,14-carbonate-baccatine V derivative,

[

Formula I

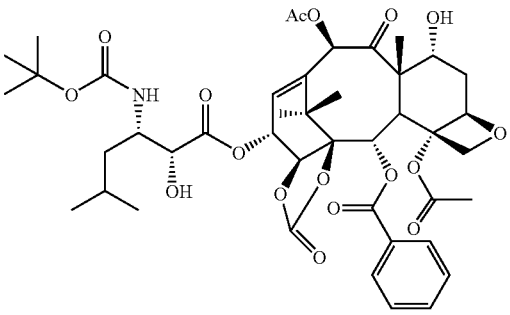

]

-continued

*Formula I*

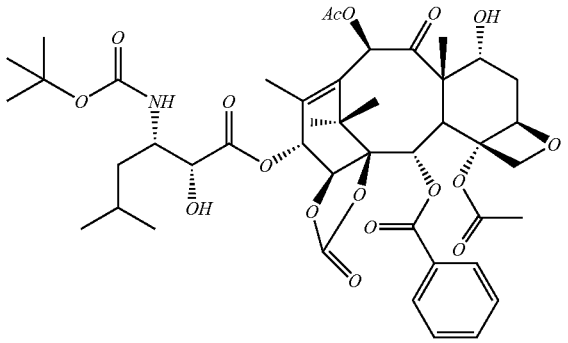

has remarkable cytotoxic and anticancer activities, and is capable of overcoming the resistance of cell lines expressing the MDR phenotype.

DETAILED DESCRIPTION OF THE PREFERRED EMBODIMENTS

The compound of the invention differs from the prior art derivatives due to the hydroxyl at the 7-position, which in the present case is in alfa configuration. 13-(N-Boc-β-Isobutylisoserinyl)-14β-hydroxy-baccatine III 1,14-carbonate, corresponding to the derivative referred to in U.S. Pat. No. 5,705,508 as SB-T-101131, can be used as starting product for the preparation of compound (I). In this case, said baccatine m derivative is either treated with DBU (diazabicyclo[5,4,0]7-undecene) in methanol or THF or it is simply left in solution with methylene chloride or chlorinated solvents in the presence of aliphatic alcohols such as methanol, ethanol or propanol with basic allumine for a time ranging from one hour to 14 days. The compound having beta configuration at C-7, is converted at neutral or slightly basic pH to the more stable alfa isomer (baccatine V derivative).

Alternatively, compound (I) can be prepared with a process which also allows to prepare the corresponding beta epimer at C-7.

Said process (A) comprises the following steps:

a) transformation of 14β-hydroxy-10-deacetylbaccatine III or V into the derivative triethylsilylated at the 7-position;

b) preparation of the 1,14 carbonate derivative from the product of step (a);

c) selective acetylation of the 10-hydroxyl;

d) reaction of the product of step (c) with (4S, 5R)-N-Boc-2-(2,4-dimethoxyphenyl)-4-isobutyl-1-oxazolidine-5-carboxylic acid;

e) cleavage of the triethylsilyl and dimethoxybenzylidene protective groups from the product of step (d).

According to a preferred embodiment of process (A), triethylchlorosilane is used as silylating agent in step (a), whereas the 1,14 carbonate derivative in step (b) is prepared using phosgene in toluene in a 3:1 methylene chloride/pyridine solution under nitrogen atmosphere. In the following step (c) 14-β-hydroxy-10-deacetylbaccatine III or V 7-Tes-1,14-carbonate is salified with LiHMDS in anhydrous THF, thereby obtaining the 10-hydroxy derivative lithium salt, which is subsequently acetylated with acetyl chloride. The condensation reaction between 14-β-hydroxy-7-Tes-1,14-carbonate-baccatine III or V and (4S, 5R)-N-Boc-2-(2,4-dimethoxyphenyl)-4-isobutyl-1-oxazolidine-5-carboxylic acid (step (d)) is carried out in anhydrous apolar organic solvent, in the presence of a base and a condensing agent such as dicyclohexylcarbodiimide (DCC).

Finally, in step (e) triethylsilyl is removed with pyridinium fluoride in acetonitrile/pyridine solution under nitrogen, whereas the dimethoxybenzylidene group is removed in methylene chloride solvent by addition of methanol HCl and subsequently of $NaHCO_3$.

The step sequence of the process described can be inverted thus obtaining the final product in as much comparable yields. Said alternative process (B) comprises the following steps:

a') selective acetylation of the hydroxyl at C-10 of 14β-hydroxy-10-deacetylbaccatine III or V;

b') preparation of the 1,14 carbonate derivative from the product of step (a')

c') silylation of the hydroxyl at C-7;

d') reaction of the product of step (c') with (4S, 5R)-N-Boc-2-(2,4-dimethoxyphenyl)-4-isobutyl-1-oxazolidine-5-carboxylic acid;

e') cleavage of the triethylsilyl and dimethoxybenzylidene protective groups from the product of step (d').

The latter process involves a number of advantages such as the possibility to obtain the desired synton (1,14-carbonate-7-Tes-baccatine III or V) without chromatographic purifications, merely by crystallization.

According to a preferred embodiment, the selective acetylation of step (a') is carried out with acetic anhydride in the presence of cerium, scandium, ytterbium salts, preferably $CeCl_3.7H_2O$, whereas the remaining steps are carried out as indicated above.

The present invention also comprises, as intermediate products of the process for the preparation of 14β-hydroxy-1,14-carbonate baccatine III or V, the following compounds: 14β-hydroxy baccatine III or V, 14β-hydroxy baccatine III or V 1,14 carbonate, 14-β-hydroxy-7-Tes-10-deacetylbaccatine III or V, 14-β-hydroxy-7-Tes-baccatine III or V, 14-β-hydroxy-7-Tes-baccatine III or V 1,14-carbonate.

A further aspect of the invention relates to a process for the preparation of (4S, 5R)-N-Boc-2-(2,4-dimethoxyphenyl)-4-isobutyl-1-oxazolidine-5-carboxylic acid, according to the following scheme:

SCHEME

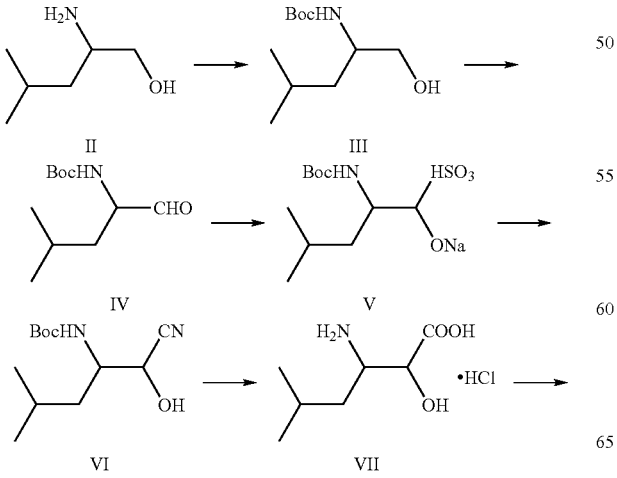

-continued

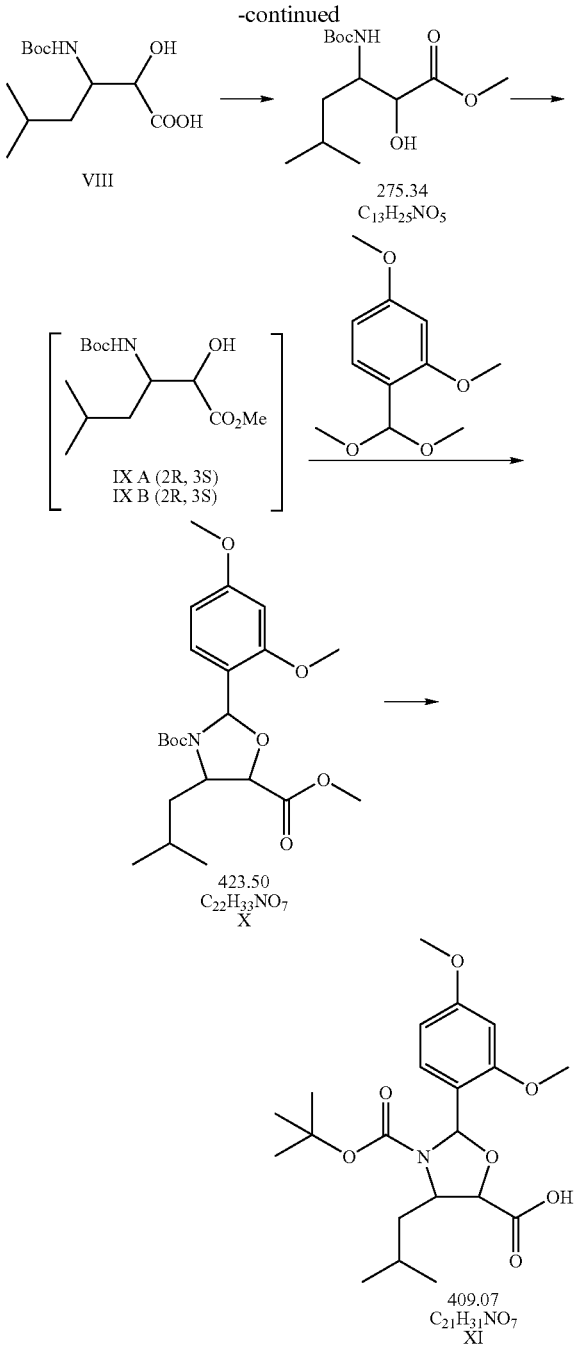

Said process comprises the following steps:

a) protection of the amino group of leucinol with Boc;

b) transformation of N-Boc-L-leucinol into N-Boc-L-leucinal;

c) preparation of the cyanhydrin of the product from step (b);

d) transformation of the cyanhydrin nitrile into the corresponding carboxylic acid;

e) formation of the carboxylic acid methyl ester;

f) purification of the (2R, 3S)-3-(N-Boc)amino-2-hydroxy-5-methylhexanoic acid methyl ester;

g) condensation of the product of step (f) with 2,4-dimethoxybenzaldehyde dimethyl acetal;

h) transformation of the (4S, 5R)-N-Boc-2-(2,4-dimethoxyphenyl)-4-isobutyl-1-oxazolidine-5-carboxylic acid methyl ester into the corresponding carboxylic acid.

According to a preferred embodiment, in step (a) leucinol is reacted with Boc-anhydride, and subsequently oxidized to aldehyde in DMSO/$CH_2Cl_2$ solvent using oxalyl chloride at a temperature below −60° C., neutralizing the formed acid with triethylamine, or oxidizing it with sodium hypochlorite at −2 to −5° C. The cyanhydrin of step (c) is prepared by substituting the sulfonic group of the intermediate 1-hydroxy-2-(N-Boc)amino-4-methylpentanesulfonate by the cyanide ion. The cyanhydrin is then hydrolyzed to the corresponding carboxylic acid in step (d) by refluxing in concentrated hydrochloric acid.

In step (e), (2R/S,3S)-3-(N-Boc)amino-2-hydroxy-5-methylhexanoic acid is converted in the corresponding methyl ester by reaction with diazomethane in ethereal solution. In step (f), diastereomer (2R, 3S) is purified by crystallization from cyclohexane or an hexane/toluene mixture. Step (g) is carried out in THF in the presence of pyridinium p-toluenesulfonate removing the developed methanol, after completion of the reaction, pyridinium p-toluenesulfonate is neutralized with bicarbonate. In step (h), the ester is hydrolysed in a methanol/water mixture with potassium carbonate. The reaction mixture is subsequently acidified and the final product is extracted with methylene chloride.

The invention also comprises (4S, 5R)-N-Boc-2-(2,4-dimethoxyphenyl)-4-isobutyl-1-oxazolidine-5-carboxylic acid as an intermediate for the synthesis of baccatine III and V derivatives substituted at the 13-position by a N-Boc-β-isobutylserinyl residue.

The novel taxane of the present invention showed a strong anticancer activity against cancerous cells of breast, lung, ovary, colon, prostate, kidney, pancreas, and also against cells resistant to the known anticancer drugs such as adriamycin, vinblastine and platinum derivatives.

Therefore, the invention relates to pharmaceutical formulations containing an effective amount of the compound of the invention, together with pharmacologically acceptable carriers and excipients. More particularly, the compound can be formulated in the form of tablets, powders, granulates, capsules, injectables, solutions, suppositories, emulsions, dispersions, and the like. For the intravenous administration, mixtures of Chemophor L and ethanol, polysorbate and ethanol or liposome formulations prepared with natural or synthetic phosphatidylcholine, or mixtures of natural phospholipids in the presence of cholesterol are mainly used; for the oral administration., soft-gelatin capsules in which the product is solubilised in polysorbates, PEG or mixtures thereof, optionally in the presence of phospholipids, are preferably prepared. Compound (I) can be administered to humans at concentrations from 50 to 500 mg/$m^2$.

The following examples illustrate the invention in greater detail.

EXAMPLE 1

Synthesis of 13-(N-Boc-β-isobutylserinyl)-14β-hydroxybaccatine III, 1,14 carbonate 43.26 g of 14β-hydroxy-deacetylbaccatine III together with 22.3 ml of N-methyl-imidazole were dissolved in 230 ml of DMF in a 500 ml glass round-bottom flask; this solution was added under strong stirring at room temperature in 1 h with 14 ml of triethylchlorosilane. When the reaction was over, the reaction mixture was poured into 2 L of water under strong stirring. An abundant precipitate formed, which was left at 4° C. overnight. The precipitate was then filtered, thoroughly washing with water and subsequently with n-hexane. After drying under vacuum 48.1 g of 7-Tes-10-deacetylbaccatine III (XII) were obtained containing a small percentage of the 7,10-derivative, having the following chemical-physical characteristics:

(XII)

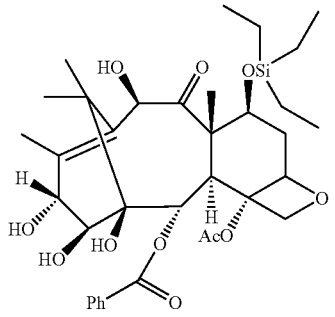

$^1$H NMR ($CDCl_3$ 200 MHz): δ (ppm) 0.55 (6H, t, J=7.8 Hz, 7-OTES $CH_2$), 0.94 (9H, q, J=7.8 Hz, 7-OTES $CH_3$), 1.18 (3H, s, C16$H_3$), 1.20 (3H, s, C17$H_3$), 1.77 (3H, s, C19$H_3$), 1.90 (1H, ddd, J=2.4, 10.8, 13.2 Hz, C6Hβ), 2.12 (3H, d, J=1.6 Hz, C18$H_3$), 2.31 (3H, s, 4-OCO$CH_3$), 2.48 (3H, ddd, J=14.3, 9.8, 6.5 Hz, C6Hα), 2.73 (1H, d, J=5.5 Hz, OH) 3.79 (1H, d, J=7.1 Hz, C3H), 4.20 (1H, dd, J=1.0, 8.3 Hz, C20Hβ), 4.31 (1H, d, J=8.6 Hz, C20Hα), 4.39 (1H, dd, J=6.4, 10.7 Hz, C7H), 4.77 (1H, d, J=5.8 Hz, C14H), 4.94 (1H, dd, J=2.1, 9.7 Hz, (C5H), 5.05 (1H, m, C13H), 5.13 (1H, d, J=1.9 Hz, C10H), 6.05 (1H, d, J=7.3 Hz, C2H), 7.41–8.09 (5H, m, Ph).

Mass Spectrum ($NH_3$, DEP/CI, positive lions): (m/z) 718 [$(M+NH_4)^+$, 100%], 701 [$(M+H)^+$, 39%].

The resulting compound was dissolved in 300 ml of a methylene chloride/pyridine 3:1 mixture under nitrogen atmosphere; this solution was added under with stirring to a phosgene solution (214 ml of a 1.9M solution in toluene) precooled at −10° C., keeping temperature from −5 to −10° C. during the addition.

The reaction mixture was stirred for 30', then shaken with 700 ml of a $NaHCO_3$ saturated solution keeping temperature below or at 2° C. The phases were separated and the organic phase was washed to remove pyridine. The organic phase was dehydrated over $MgSO_4$ and concentrated to dryness 46.6 g of 10-deacetylbaccatine III 7-Tes-1,14-carbonate were obtained which could be directly used for the following reactions.

31 g of the compound were dissolved in 250 ml of strictly anhydrous THF; the solution was cooled at −50° C. and added with 48 ml of a 1M LiHMDS solution in 2 minutes and stirred for 20 minutes at the same temperature. 3.7 g of acetyl chloride were added during 40 min. with stirring. The reaction temperature was left to raise to 0° C. keeping stirring for 2 h. Upon completion of the reaction, the mixture was treated with a $NH_4Cl$ saturated solution and diluted with ethyl acetate. The phases were separated and the aqueous solution was diluted with ethyl acetate until exhaustion of the product. The combined organic phases were washed with water then dried over $MgSO_4$ and concentrated to dryness. 33 g of 14β-hydroxy-7-Tes-1,14-carbonate-baccatine III were obtained, impure due to the compounds of the preceding reactions. This compound was chromatographed on silica gel eluting the pure product with an ethyl acetate/$CH_2Cl_2$ 9:1 mixture. 30 g of the desired product (XIII) were obtained, having the following characteristics:

(XIII)

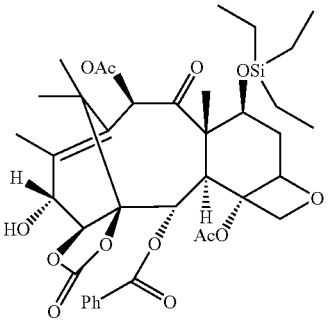

$^1$H NMR ($CDCl_3$ 200 MHz): δ (ppm)=0.55 (6H, t, J=7.8 Hz, 7-OTES $CH_2$), 0.95 (9H, q, J=7.8 Hz, 7-OTES $CH_3$), 1.16 (3H, s, C16$H_3$), 1.32 (3H, s, C17$H_3$), 1.77 (3H, s, C19$H_3$), 1.88 (1H, ddd, J=2.4, 10.8, 13.2 Hz, C6Hβ), 2.21 (3H, d, J=1.6 Hz, C18$H_3$), 2.19 (3H, s, 10-OCO$CH_3$), 2.31 (3H, s, 4-OCO$CH_3$), 2.48 (3H, ddd, J=14.3, 9.8, 6.5 Hz, C6Hα), 2.73 (1H, d, J=5.5 Hz, OH) 3.72 (1H, d, J=7.1 Hz, C3H), 4.20 (1H, d, J=8.3 Hz, C20Hβ), 4.31 (1H, d, J=8.6 Hz, C20Hα), 4.46 (1H, dd, J=6.4, 10.7 Hz, C7H), 4.79 (1H, d, J=5.8 Hz, C14H), 4.94 (1H, dd, J=2.1, 9.7 Hz, (C5H), 5.02 (1H, m, C10H), 5.05 (1H, m, C13H), 6.09 (1H, d, J=7.3 Hz, C2H), 7.41–8.09 (5H, m, Ph).

Mass Spectrum ($NH_3$, DEP/CI, positive ions): (m/z) 759 [$(M+NH_4)^+$, 19%], 743 [$(M+H)^+$, 100%].

20 g of 14β-hydroxy-7-Tes-1,14-carbonate-baccatine III together with a 300 ml of strictly anhydrous toluene were placed in a 1 L round-bottom flask, 10 g of (4S, 5R)-N-Boc-2-(2,4-dimethoxyphenyl)-4-isobutyl-1-oxazoli-dine-5-carboxylic acid and 2 g of N,N-dimethylaminopyridine (DMAP) and 9.5 g of dicyclohexylcarbodiimide (DCC) dissolved in $CH_2Cl_2$ were added. The reaction mixture was refluxed for 3 h, then cooled, the ureic product was precipitated off and mother liquors were washed with a $NaHCO_3$ saturated solution to remove the unreacted acid, then with diluted hydrochloric acid to remove DMAP and finally again with $NaHCO_3$ to neutrality. The organic phase was concentrated to dryness to obtain 41.5 g of product which could be directly used in the subsequent step.

40 g of this compound were deprotected in two steps, by removing first Tes and then 2,4-dimethoxybenzaldehyde. 40 g of the compound were dissolved in 100 ml of an acetonitrile/pyridine mixture (80:100) under nitrogen and cooled at 0° C.; 13 ml of pyridinium fluoride were added and the whole was left under stirring for 24 h. The solution was poured into 2 L of water and the product was filtered and dried under vacuum.

The residue was dissolved in 60 ml of methylene chloride and this solution was added with 40 ml of 0.6N HCl in methanol under strong stirring and at 0° C. The reaction mixture was left for 2 h under stirring, then diluted with 150 ml of methylene chloride and shaken with a $NaHCO_3$ solution adjusting pH to 6–7. The organic phase was concentrated to dryness and the residue was crystallized from acetone hexane. After drying, 16 g of 13-(N-Boc-β-isobutylisoserinyl)-14β-hydroxybaccatine-1,14-carbonate were obtained, having the following chemico-physical and spectroscopical characteristics:

Formula: $C_{44}H_{57}NO_{17}$

Aspect: white powder.

Melting point: 245° C.

TABLE 1

Chemical shifts (ppm) $^1$H NMR in $CDCl_3$ solution (200 MHz)

| H | Ppm, multiplicity (Hz) | H | Ppm, multiplicity (Hz) |
|---|---|---|---|
| 2 | 6.09-d (7.8) | 2' | 4.30-dd (6.4; 3.2) |
| 3 | 3.68-d (7.4) | 3' | 4.08-m |
| 5 | 4.91-dd (9.7; 2.5) | 4'a | 1.21-m |
| 6α | 2.52-ddd (14.8; 9.8; 6.9) | 4'b | 1.43-m |
| 6β | 1.86-m | 5' | 1.65-m |
| 7 | 4.37-m | 6' | 0.96-d (6.3) |
| 10 | 6.25-s | 7' | 0.95-d (6.3) |
| 13 | 6.44-d (broad, 6.9) | 4-OCOC$\underline{H}_3$ | 2.40-s |
| 14 | 4.84-d (6.9) | 10-OCOC$\underline{H}_3$ | 2.22-s |
| 16 | 1.25-s | Boc | 1.35-s |
| 17 | 1.32-s | o-benzoyl | 8.01-m |
| 18 | 1.87-d (1.6) | m-benzoyl | 7.46-m |
| 19 | 1.69-s | p-benzoyl | 7.58-m |
| 20α | 4.27-d (8.4) | 3-NH | 4.72-d (9.0) |
| 20β | 4.20-d (8.4) | | |

TABLE 2

Chemical shifts (ppm) $^{13}$C NMR in $CDCl_3$ solution (50.308 MHz)

| C | ppm, multiplicity | C | ppm, multiplicity |
|---|---|---|---|
| 9 | 201.8-s | 8 | 58.2-s |
| 1' | 172.6-s | 3' | 51.2-d |
| 4-O$\underline{C}$OCH$_3$ | 170.5-s | 3 | 44.6-d |
| 10-O$\underline{C}$OCH$_3$ | 170.2-s | 15 | 41.3-s |
| 2-$\underline{C}$OPh | 164.3-s | 4 | 39.9-t |
| $\underline{C}$—O (Boc) | 155.8-s | 6 | 34.9-t |
| $\underline{C}$═O (carbonate) | 151.4-s | ($\underline{C}$H$_3$)$_3$C Boc | 27.7-q |
| 12 | 139.4-s | 17 | 25.5-q |
| 11 | 133.1-s | 16 | 22.6-q |
| (Me)$_3\underline{C}$ (Boc) | 80.0-s | 4-OCO$\underline{C}$H$_3$ | 22.0-q |
| 5 | 83.8-d | 10-OCO$\underline{C}$H$_3$ | 20.2-q |
| 1 | 87.7-s | 5' | 24.3-d |
| 4 | 80.0-s | 6' | 22.7-q |
| 2 | 69.0-d | 7' | 21.6-q |
| 20 | 75.5-t | 18 | 14.6-q |
| 2' | 73.3-d | 19 | 9.8-q |
| 7 | 71.2-d | q-benzoyl | 127.5-s |
| 10 | 74.3-d | o-benzoyl | 129.5-d |
| 13 | 74.1-d | m-benzoyl | 128.6-d |
| 14 | 79.1-d | p-benzoyl | 133.7-d |

Mass Spectra: ($NH_3$, DEP/CI, positive ions): (m/z) 889 [$(MNH_4)^+$], 832 [$(MNH_4$—$(CH_3)_3C)^+$], 772 [$(MNH_4$—$BocNH_2)^+$].

($NH_3$, DEP/CI, negative ions): (m/z) 871 ($M^-$), 260 (side chain)

Infrared Spectrum (KBr disc): 3521, 3321, 2971, 2953, 1826, 1762, 1706, 1526, 1366, 1238, 1165, 1072, 723 $cm^{-1}$ UV Spectrum (MeOH): 231, 276 and 284 nm;

$E_{1\%}$ at 231 nm=180.99

$E_{1\%}$ at 276 nm=14.094

$E_{1\%}$ at 284 nm=12.182

EXAMPLE 2

Synthesis of 13-(N-Boc-β-isobutylserinyl)-14β-hydroxybaccatine V, 1,14 carbonate 5 g of 13-(N-Boc-β-isobutylserinyl)-14β-hydroxybaccatine III, 1,14 carbonate were dissolved in 500 ml of toluene under argon atmosphere, completely deoxygenating the solution; 80 mg of DBU (diazabicyclo[5,4,0]7-undecene) were added and the reaction mixture was refluxed for 1 hour under argon atmosphere. The solution was diluted with 100 ml of ethyl acetate and washed with water. The organic phase was evaporated to dryness to obtain 4.5 g of 13-(N-Boc-13-isobutylserinyl)-14β-hydroxybaccatine V 1,14 carbonate having the following chemical-physical and spectroscopical characteristics:

Formula: $C_{44}H_{57}NO_{17}$

Aspect: white powder

Melting point: 245° C.

TABLE 3

Chemical shift (ppm) $^1$H NMR in $CDCl_3$ solution (200 MHz)

| H | Ppm, multiplicity (Hz) | H | Ppm, multiplicity (Hz) |
|---|---|---|---|
| 2 | 6.18 d (7.9) | 2'* | 4.75 d (8.6) |
| 3 | 3.80 d (7.8) | 3' | 4.01 m |
| 5 | 4.93 dd (7.8; 4.8) | 4'a | 1.25 m |
| 6 | 2.23 m | 4'b | 1.48 m |
| 7 | 3.76 m | 5' | 1.67 m |
| 10 | 6.79 s | 6' | 0.99 d (6.4) |
| 13 | 6.44 d (6.7) | 7' | 0.97 d (6.4) |
| 14 | 4.88 d (7.0) | 4-OCOC$\underline{H}_3$ | 2.58 s |
| 16 | 1.29 s | 10-OCOC$\underline{H}_3$ | 2.20 s |
| 17 | 1.31 s | Boc | 1.37 s |
| 18 | 1.87 d (1.5) | o-benzoyl | 8.06 m |
| 19 | 1.71 s | m-benzoyl | 7.49 m |
| 20 | 4.38 s | p-benzoyl | 7.61 m |
| | | 3'-NH* | 4.60 d (11.2) |

*Can be reversed

TABLE 4

Chemical shift (ppm) $^{13}$C NMR in $CDCl_3$ solution (50.308 MHz)

| C | Ppm, multiplicity | C | Ppm, multiplicity |
|---|---|---|---|
| 9 | 206.1 s | 8 | 58.2 s |
| 1' | 173.1 s | 3' | 52.0 d |
| 4-O$\underline{C}$OCH$_3$ | 172.7 s | 3 | 40.4 d |
| 10-O$\underline{C}$OCH$_3$ | 169.3 s | 15 | 41.5 s |
| 2-$\underline{C}$OPh | 165.1 s | 4' | 40.6 t |
| $\underline{C}$=O (Boc) | 156.6 s | 6 | 35.2 t |
| $\underline{C}$—O (Carbonate) | 152.1 s | ($\underline{C}$H$_3$)$_3$C (Boc) | 28.4 q |
| 12 | 137.6 s | 17 | 25.4 q |
| 11 | 134.0 s | 16 | 22.4 q |
| (Me)$_3\underline{C}$ (Boc)§ | 81.7 s | 4-OCO$\underline{C}$H$_3$ | 22.7 q |
| 5 | 82.7 d | 10-OCO$\underline{C}$H$_3$ | 18.6 q |
| 1 | 88.5 s | 5' | 25.1 d |
| 4§ | 80.7 s | 6' | 23.4 q |
| 2 | 69.9 d | 7' | 20.9 q |
| 20 | 77.2 t | 18 | 15.2 q |
| 2'° | 74.6 d | 19 | 16.2 q |
| 7° | 77.6 d | q-benzoyl | 128.3 s |
| 10° | 74.2 d | o-benzoyl | 160.2 d |
| 13° | 76.0 d | m-benzoyl | 128.2 d |
| 14 | 79.9 d | p-benzoyl | 134.4 d |

*, §, °, = Can be reversed

Mass Spectrum (TSP+): (m/z) 872 ($MH^+$); 816 ($MH_+$—$(CH_3)_2$=$CH_2$); 772 (816-$CO_2$); 756 (816-AcOH); 712 (772-AcOH)

Infrared Spectrum (KBr disc): 3450, 2963, 1813, 1740, 1702, 1247, 1091, 710 $cm^{-1}$ UV Spectrum (MeOH): 200 e 230 nm $E_{1\%}$ at 200 nm=370.9

$E_{1\%}$ at 230 nm=193.2

EXAMPLE 3

Preparation of (4S, 5R)-N-Boc-(2,4-dimethoxyphenyl)-4-isobutyl-1-oxazolidine-5-carboxylic acid Preparation of N-Boc-L-leucinol (III):

46.8 g of L-leucinol II (400 mmol) were dissolved in 300 ml of $CH_2Cl_2$ in a 2 l three-necked round-bottom flask equipped with mechanical stirrer, thermometer and dropping funnel. The stirred solution was then added drop by drop at room temperature with the solution of Boc anhydride (87.2 g, 400 mmol) in $CH_2Cl_2$ (100 mL) in 90 minutes. During the addition of the first 25% of Boc-anhydride, the reaction was exothermic and it reached 20–30° C. yielding a slurry which turned clear after stirring at room temperature for a further three hours. The whole was left at room temperature overnight. The solvent was evaporated under high vacuum to obtain the desired product as a thick oil in a quantitative yield (87 g). The product was subsequently treated without further purification.

Preparation of N-Boc-L-leucinal (IV)

A solution of oxalyl chloride (26.274 mL, 300 mmol) in 130 ml of methylene chloride precooled at −60/−65° C. was slowly added with DMSO (28.4 mL, 400 mmol).

The solution turned clear when the addition of DMSO was completed. After 20 minute stirring at the same temperature the reaction mixture was subsequently treated with a solution of alcohol III (43.7 g, 200 mmol) in $CH_2Cl_2$ (200 mL) for 25 min keeping temperature below −60° C. During the addition of the alcohol the reaction mixture became cloudy, and a white precipitate formed. After 20–25 minutes of stirring at the same temperature a solution of triethylamine (112 mL, 800 mmol) in $CH_2Cl_2$ (100 mL) was added dropwise in 40 minutes keeping temperature between −68 and −62° C. The reaction mixture was then stirred at between −60 and −65° C. for a further 50 minutes. TLC of the reaction mixture carried out using 8% methanol in $CH_2Cl_2$ as eluent detected no starting product.

The cold solution was then poured into 800 ml of an iced solution containing 68 g (0.5 mol) of $KHSO_4$. The organic layer was separated and the aqueous phase extracted with $CH_2Cl_2$ (100 mL). The combined organic phases were washed with aqueous $KHSO_4$ (5%, 1×200 mL), brine (100 mL, 50 mL) and concentrated to half volume (−250 mL). Said material was used directly in the subsequent step.

Aldehyde (V) Bisulfite Compound Derivative

The methylene chloride solution of the aldehyde (IV) in a 2 l three-necked round-bottom flask equipped with mechanical stirrer, thermometer and dropping funnel was treated in 10 minutes and at −5° C. with a sodium solution bisulfite (41.7 g, 400 mmol) in water (200 mL) and subsequently with n-$Bu_4NHSO_4$ (678 mg, 2 mmol). The solution was cooled to −5° C. The reaction mixture was stirred at −5 to −0° C. for 5–6 hours and subsequently overnight at room temperature. The aqueous phase containing compound V was separated and washed with $CH_2Cl_2$ (2×20 mL).

(2-Cyano-3-(N-Boc)-amino-5-methyl-hexanol (VI)

The above aqueous solution (-250 mL) was added with $CH_2Cl_2$ (120 mL) and the reaction mixture was cooled to 0–5° C. on an ice bath. Solid KCN (15 g, 230 mmol) was subsequently added to the reaction mixture and the solution was stirred at room temperature overnight. The organic phase was separated and the aqueous phase was extracted with $CH_2Cl_2$. The combined organic phases were washed with brine (1×50 mL), dried over $MgSO_4$ and evaporated to obtain the product as a colourless viscous liquid (43 g). The product had $[\alpha]_D$ 51.11 (c=2, MeOH) and was an about 2:1 mixture of the VI 2(R),3(S) and 2(S),3(S) derivatives. The yield was 89% compared with the starting L-leucinol.

(2RS,3S)-3-Amino-2-hydroxy-5-methylhexanoic acid (VII)

The mixture of the above crude nitrile VI (43 g) was treated with 150 ml of concentrated HCl (37%) (150 mL)

and refluxed overnight to give the crude acid VII*. The hydrochloric acid excess was removed by rotatory evaporator and the residue was evaporated with water (100 ML) to remove HCl. The residue was then dissolved in 150 ml of water and added with 100 ml of acetone, then treated with 33 ml of a 6.25M NaOH solution to adjust pH to 5. A further amount of acetone (500 mL) was then added to the solution which was left to stand overnight at 4° C. The precipitated solid was subsequently filtered and the solid cake was washed with acetone and dried under vacuum to give crude acid VII (6.5 g) containing an about 3:1 mixture of 2(R),3(S) and 2(S),3(S) derivatives of compound VI.

The filtrate was evaporated and water was added to adjust the volume of the solution to 75 mL.

Acetone (1 L) was then added to the solution which was left to stand overnight at 4° C. in refrigerator. The precipitated solid was then filtered and the solid cake was washed with acetone and dried under vacuum to give a second amount of product (18 g) containing solid NaCl with an about 1:1 mixture of 2(R),3(S) and 2(S),3(S) derivatives of VII.

The first product VII recovered (22.5 g) was heated in water (120 mL) without obtaining a complete dissolution and then cooled in ice and filtered to obtain 12.5 g of acid VII still contaminated by about 10 of undesired 2(R),3(S) derivative of VII. This product was dried and mixed with the above 1:1 mixture of the second crop crystals (total ~27 g)

(2RS,3S)-3-(N-Boc)Amino-2-hydroxy-5-methylhexanoic acid (VIII)

(A) The crude acid VI 2(R),3(S), about 90% purity, (2.5 g, 77.6 mmol) was dissolved in a water-THF 1:1 mixture (80 ML), then triethylamine (13.5 mL) and subsequently Boc anhydride (18.5 g, 85 mmol) were added to the reaction mixture, the whole solution was stirred for 40 hours at room temperature. The solvent was evaporated by rotatory evaporator, 60 ml of water and 60 ml of ethyl acetate were added keeping the whole under stirring. The aqueous phase was separated and extracted with ethyl acetate (30 mL). The combined organic phases were extracted with 10% aqueous sodium carbonate (30 mL, 20 mL). The basic extract was then combined with an aqueous phase acidified with 2M hydrochloric acid (~55 mL) to adjust pH of the solution to 2. Acid VIII was then extracted from the aqueous phase with ethyl acetate (3×40 mL) and the heteroacetic extracts were washed with water (20 mL), dried ($MgSO_4$) and evaporated to give the crude VIII Boc derivative as syrup (20 g, 99%).

(B) The crude acid VII 2R,3S, with purity of about 50%, contaminated by NaCl (27 g), was dissolved in a water-dioxane 1:1 mixture (120 mL). Triethylamine (20 mL) was then added to the reaction mixture, then Boc anhydride (26.16 g, 120 mmol). The solution was stirred for 40 hours at room temperature. The solvent was evaporated by rotatory evaporator and water (100 mL) and ethyl acetate (100 mL) were added to the residue keeping stirring for a further few minutes. The organic phase was separated and extracted with 10% aqueous sodium carbonate (45 mL, 30 mL). The sodium carbonate extracts were then combined with the aqueous phase, acidified with 1M hydrochloric acid (~165 mL) and extracted with ethyl acetate (3×60 mL), afterwards washed with water (30 mL), dried ($MgSO_4$) and evaporated to give the crude VII Boc as syrup (16 g), consisting of a 1:1 mixture of the 2R,3S and 2S,3S isomers.

(2R,3S)-3-(N-Boc)Amino-2-hydroxy-5-methylhexanoic acid methyl ester (IX)

Diazomethane was prepared from diazald following the process reported in T. H. Black [Aldrichimica Acta, 16, 3 (1983)].

(A) A solution of the crude acid VIII (20 g, 56.6 mmol) in $CH_2Cl_2$ (75 mL) was slowly added to a cold diazomethane ethereal solution (~77 mmol) and the mixture was left for two hours on ice bath. The colour of the solution in that step turned white thus indicating that most diazomethane had been adsorbed. The solution was then concentrated and the residue crystallized from a mixture of toluene (20 mL) and hexane (70 mL). After cooling overnight in refrigerator at 4° C., the crystals of the pure IXA 2R,3S derivative were collected by filtration. The yield was 15 g. The mother liquors gave about 5 g of a 1:1 isomeric mixture.

(B) Using the same procedure, a 1:1 mixture of acid VIII (16 g) was transformed into a 1:1 mixture of IXA and IXB esters. The material from mother liquors (5 g from step A) was added and the material was combined and separated by column chromatography using hexane-ethyl acetate as eluent (9:1 to 7:3). Ninhydrine was used as developer for the TLC plates. The apolar compound, Rf 0.75 (hexanoethyl acetate: 7:3) was identified as the desired ester IXA (2R,3S), which was recrystallized from cyclohexane to give IXA as colorless needles (8 g) m.p. 95–96° C., $[\alpha]_D$ 72.4° (c=1, MeOH).

The polar compound, Rf 0.5 (hexane-ethyl acetate 7:3) was identified as IXB (2S,3S) and was recrystallized from cyclohexane to give 10 g of IXB as colorless needles.

2,4-dimethoxybenzaldehydedimethyl acetal

A mixture of 2,4-dimethoxybenzaldehyde (41.25 g, 0.25 mols), anhydrous trimethyl orthoformate (50 mL) and ammonium nitrate (2 g dissolved in 20 ml of methanol) was refluxed for 6 hours ($^1$HNMR of the reaction mixture showed a 65–70% conversion). At first, the hot reaction mixture was a clear solution, but as the reaction progressed the solid precipitated. A second portion of anhydrous trimethyl orthoformate (20 mL) was added and part of methanol was distilled off.

When the temperature of the reaction mixture reached 95–100° C., all the solid dissolved in the flask. The solution was cooled to room temperature and added with anhydrous $Na_2CO_3$ (5 g), stirring for 30 min. Subsequently the solution was filtered and the residue was distilled by fractional distillation under vacuum at 0.25 mmHg. The first fraction at low temperature mainly consisted of the trimethyl orthoformate excess and the second fraction, which distilled as colourless oil at 175–180° C., was the desired acetal. Yield: 37 g (70%).

(4S,5R)-N-Boc-2-(2,4-Dimethoxyphenyl)-4-isobutyl-1-oxazolidine-5-carboxylic acid methyl ester (X)

A solution of (2R, 3S)-3-(N-Boc)amino-2-hydroxy-5-methylhexanoic acid methyl ester (IXA) (34.375 g, 125 mmol) in anhydrous THF (150 ml) was added with distilled 2,4-dimethoxybenzaldehyde dimethyl acetal (30 g, 142 mmol) and subsequently pyridinium p-toluenesulfonate (Py.Tos; 400 mg).

The solution was heated under mild reflux in a 500 ml three-necked flask equipped with a Dean-Stark separator. After about 6 hours under reflux, about 60 ml of THF containing methanol generated during the reaction were removed. A sample was taken for $^1$H NMR analysis (in $CDCl_3$). The peak at δ=1.41 ppm disappeared (1) and a novel peak appeared at δ=1.24 ppm for the protected methyl ester (2). After 6 hour reflux, the conversion was about 70–75%.

A fresh aliquot of anhydrous THF (50 ml) was added, then an amount of 2,4-dimethoxybenzaldehyde acetal (5.0 g; 24 mmol). The reaction mixture was refluxed for a further 2.5 hours, during which time about 50 ml of THF were removed using the Dean-Stark apparatus. The subsequent $^1$H NMR analysis showed the complete transformation of the starting material.

The reaction mixture was added with a $NaHCO_3$ saturated aqueous solution (15 ml) and the mixture was stirred for 15 minutes to neutralize Py.Tos. t-Butyl methyl ether (85 ml) and water (15 ml) were subsequently added and the organic phase was separated. The aqueous phase was extracted with t-butyl methyl ether (20 ml) and the combined organic phases were washed with water (30 ml) and evaporated to a residue (66 g) of crude product X.

Hydrolysis of Ester X to Give Acid XI

The crude ester X (22 g, 42 mmol) was dissolved in 100 ml of methanol and added with water (50 ml) containing 8.7 g of potassium carbonate. After stirring overnight at room temperature, the reaction was considered completed by TLC monitoring (toluene-ethyl acetate: 4.5:1). TLC analysis was confirmed by $^1H$ NMR analysis, checking the disappearance of the methyl ester peak.

Methanol was evaporated at a temperature not above 40° C. under vacuum (about 60 g residue) and water (150 ml) was added to the residue. The aqueous suspension was extracted with ethyl acetate (5×50 ml) to remove the benzaldehyde and benzaldehyde dimethyl acetal excess. 90 ml of methylene chloride were added to the aqueous phase, the mixture was cooled on ice bath and the diphasic system was treated with about 125 ml of 1M $NaHSO_4$ (pH=3) under strong stirring. The phases were separated and the aqueous phase was extracted with methylene chloride (75 ml). The combined methylene chloride extracts were washed with water (30 ml), brine (30 ml) and dried over $MgSO_4$. The solution was then kept at −60° C. until next use. The yield in the final product as colourless solid was of 16 g, about 93% based on the starting product.

EXAMPLE 4

Preparation of 14β-hydroxy-7-Tes baccatine III 1,4 carbonate

A solution of 11.2 g of 10-deacetyl-14-hydroxybaccatine III in 50 ml of dry tetrahydrofuran was added with 0.72 g of $CeCl_3.7H_2O$ and 7.3 ml of acetic anhydride. The reaction mixture was stirred at room temperature for 5 hours; during this time the mixture became homogeneous. 10 g of ice were added and the whole was stirred for 1 hour. Tetrahydrofuran was evaporated off under vacuum and the residue was diluted with 200 ml of $H_2O$. The precipitate was filtered and dried under vacuum in the presence of $P_2O_5$; the product was crystallized from ethyl acetate to obtain 10 g of 14-hydroxybaccatine III having the following characteristics:

Mp: 236–8° C.; IR (KBr): 3474, 1739, 1400, 1240, 1090, 1049 $cm^{-1}$.

$^1H$ NMR ($CDCl_3$, 200 MHz); 8.07 (d, J=8 Hz, Bz), 7.55 (d, J=8 Hz, Bz), 7.44 (t, J=8 Hz, Bz), 6.31 (s, H-10), 5.80 (d, J=7 Hz, H-2), 4.97 (br d, J=8 Hz, H-5), 4.73 (br, d, J=4 Hz, H-13), 4.41 (m, H-7), 4.24 (d, J=4 Hz, H-14), 4.20 (d, J=7 Hz, H-20a), 4.06 (d, J=7 Hz, H-20b), 3.89 (J 0 (Hz, H-3), 2.29 (s, OAc), 2.22 (s, OAc), 2.04 (s, H-18), 1.66 (s, H-19), 1.25, 1.11 (s, H-16 and H-17).

In a four-necked flask equipped with stirrer, dropping funnel, thermometer and reflux condenser cooled to −12° C., were placed 52.8 ml of a 1.9M solution of phosgene in toluene. This solution was dropwise added with 11.6 g of 14-hydroxy baccatine III dissolved in 53 ml of methylene chloride and 17.5 ml of pyridine under stirring in 30 minutes. Temperature was kept between −6 and −10° C. After 30 minutes 50 ml of $NaHCO_3$ saturated solution were added under stirring keeping a tight control of the temperature. After warming to room temperature, the phases were separated. The aqueous phase was contraextracted with methylene chloride and the organic phases were washed with 45 ml of 2N HCl adjusting pH to about 1. The organic phase was washed with 0.1N HCl and then with $NaHCO_3$, then dried over $Na_2SO_4$ and evaporated to dryness to quantitatively obtain 11.5 g of 14-hydroxybaccatine-1,14 carbonate.

11.5 g of 14-hydroxybaccatine-1,14 carbonate were dissolved in 50 ml of DMF and 1 l equivalents of chlorotriethylsilane and 3 equivalents of N-methyl-imidazole were added at room temperature. After completion of the reaction, the mixture was poured into 500 ml of $H_2O$ and the precipitate was filtered and washed thoroughly with $H_2O$, then dried to obtain 12.8 g of 14β-hydroxy-7-Tes-baccatine III-1, 14 carbonate with the same characteristics as those reported in example 1.

EXAMPLE 5

Synthesis of 13-(N-Boc-L-isobutylserinyl)-14β-hydroxybaccatine III, 1,14 carbonate Starting from 14β-hydroxy-7-Tes-baccatine III-1,14 carbonate obtained as described in the above example, the procedure was as follows.

In a 1 L round-bottom flask were placed 20 g of 14β-hydroxy-7-Tes-1,14-carbonate-baccatine III together with 300 ml of strictly anhydrous toluene; 10 g of (4S, 5R)-N-Boc-2-(2,4-dimethoxyphenyl)-4-isobutyl-1-oxazolidine-5-carboxylic acid dissolved in $CH_2Cl_2$ and 2 g of N,N-dimethylaminopyridine (DMAP) were added and 9.5 g of dicyclohexylcarbodiimide (DCC) were added. The reaction mixture was refluxed for 3 h, then cooled to precipitate off the ureic product and mother liquors were washed with a $NaHCO_3$ saturated solution to remove the unreacted acid, then with diluted hydrochloric acid to remove DMAP and finally again with $NaHCO_3$ to neutrality. The organic phase was concentrated to dryness to obtain 41.5 g of product which could be directly used in the subsequent step.

40 g of this compound were deprotected in two steps by cleaving first Tes and then 2,4-dimethoxybenzaldehyde. 40 g of the compound were dissolved in 100 ml of an acetonitrile/pyridine mixture (80:100) under nitrogen and the mixture was cooled to 0° C.; 13 ml of pyridinium fluoride were added and the whole was left under stirring for 24 h. The solution was poured into 2 L of water and the product was filtered and dried under vacuum. The residue was dissolved in 60 ml of methylene chloride and this solution was added with 40 ml of Methanol HCl 0.6N under strong stirring and at 0° C. The reaction mixture was left for 2 h under stirring, then diluted with 150 ml of methylene chloride and shaken with a $NaHCO_3$ solution adjusting pH to 6–7. The organic phase was concentrated to dryness and the residue was crystallized from acetone hexane, then dried to obtain 16.5 g of 13-(N-Boc-β-isobutylisoserinyl)-14β-hydroxybaccatine III 1,14-carbonate.

What is claimed is:

1. A compound of Formula I,

[ Formula I

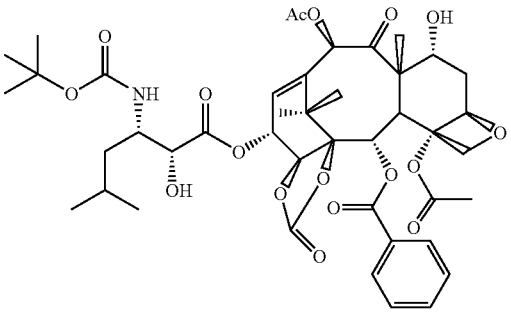

]

Formula I

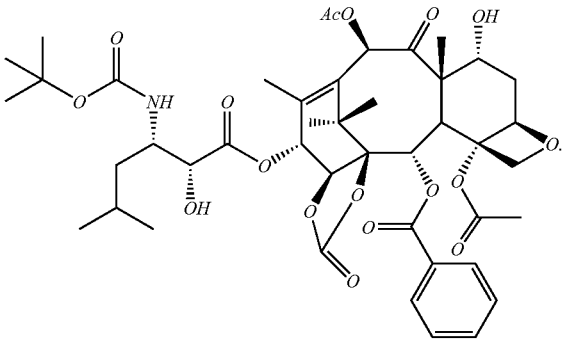

2. A process for preparing a compound of Formula I,

[ Formula I

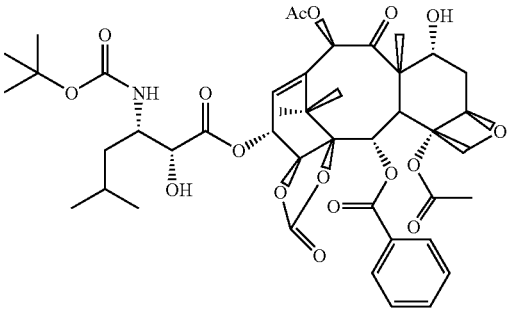

]

Formula I

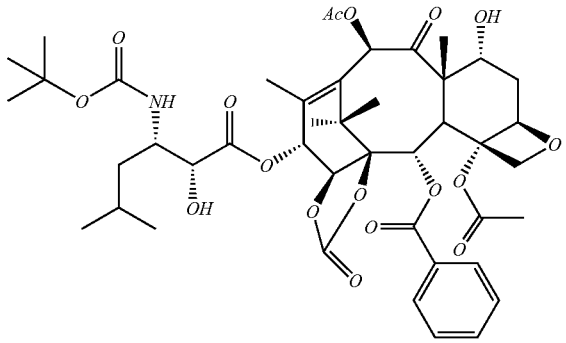

comprising reacting 13-(N-Boc-β-isobutylisoserinyl)-14β-hydroxy-baccatine III 1,14-carbonate with diazabicyclo[5,4,0]7-undecene in methanol or THF.

3. A method of treating cancer [selected from the group consisting of breast, ovarian and colon cancer] in a patient in need thereof comprising administering to [said] *a* patient *having breast, ovarian, or colon cancer* a therapeutically effective amount of a compound of claim 1.

4. The method of claim 3, wherein the compound is administered in an amount [of] from 50 to 500 mg/m$^2$.

5. A pharmaceutical composition comprising the compound of claim 1 and one or more pharmaceutically acceptable carriers and/or excipients.

6. The method of claim 3 wherein the cancer is breast cancer.

7. The method of claim 3 wherein the cancer is ovarian cancer.

8. The method of claim 3 wherein the cancer is colon cancer.

*9. A process for preparing a compound of Formula I,*

*Formula I*

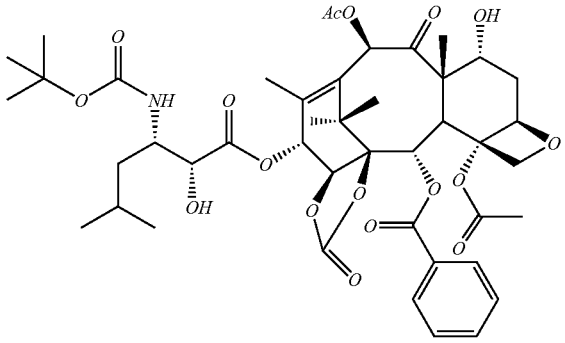

*comprising preparing (4S, 5R)-N-Boc-2-(2,4-dimethoxyphenyl)-4-isobutyl-1-oxazolidine-5-carboxylic acid, comprising the steps of:*

*a. protecting the amino group of a leucinol with Boc to form N-Boc-L-leucinol;*

*b. converting the N-Boc-L-leucinol into N-Boc-L-leucinal;*

*c. preparing a cyanhydrin nitrile from the N-Boc-L-leucinal;*

*d. transforming the cyanhydrin nitrile into a carboxylic acid;*

*e. forming a methyl ester of the carboxylic acid;*

*f. purifying the methyl ester of the carboxylic acid;*

*g. condensing the product of step (f) with 2,4-dimethoxybenzaldehyde dimethyl acetal to form (4S, 5R)-N-Boc-2-(2,4-dimethoxyphenyl)-4-isobutyl-1-oxazolidine-5-carboxylic acid methyl ester;*

*h. transforming the (4S, 5R)-N-Boc-2-(2,4-dimethoxyphenyl)-4-isobutyl-1-oxazolidine-5-carboxylic acid methyl ester into the (4S, 5R)-N-Boc-2-(2,4-dimethoxyphenyl)-4-isobutyl-1-oxazolidine-5-carboxylic acid; and*

*i. using the (4S, 5R)-N-Boc-2-(2,4-dimethoxyphenyl)-4-isobutyl-1-oxazolidine-5-carboxylic acid to prepare the compound of Formula I.*

*10. The process of claim 2, wherein the 13-(N-Boc-β-isobutylisoserinyl)-14β-hydroxy-baccatine III 1,14-carbonate is prepared by a process comprising the steps of:*

*a. reacting 14β-hydroxy-10-deacetylbaccatine III with a silylating agent to provide a 7-triethylsilyl 14β-hydroxy-10-deacetylbaccatine III;*

*b. reacting the 7-triethylsilyl 14β-hydroxy-10-deacetylbaccatine III with phosgene to provide a 1,14 carbonate 7-triethylsilyl 14β-hydroxy-10-deacetylbaccatine III;*

*c. reacting the 1,14 carbonate 7-triethylsilyl 14β-hydroxy-10-deacetylbaccatine III with a LiHMDS to provide a*

*lithium salt of the 10-hydroxyl group of the 1,14 carbonate 7-triethylsilyl 14β-hydroxy-10-deacetylbaccatine III;*

*d. reacting the lithium salt of the 10-hydroxyl group of the 1,14 carbonate 7-triethylsilyl 14β-hydroxy-10-deacetylbaccatine III with an acetylating agent to acetylate the 10-hydroxyl group to provide a 1,14 carbonate 7-triethylsilyl 14β-hydroxy-10-acetylbaccatine III;*

*e. reacting the 1,14 carbonate 7-triethylsilyl 14β-hydroxy-10-acetylbaccatine III with (4S, 5R)-N-Boc-2-(2,4-dimethoxyphenyl)-4-isobutyl-1-oxazolidine-5-carboxylic acid to form a C-13 esterified 1,14 carbonate 7-triethylsilyl 14β-hydroxy-10-acetylbaccatine III; and*

*f. removing the 7-triethylsilyl group from the C-13 esterified 1,14 carbonate 7-triethylsilyl 14β-hydroxy-10-acetylbaccatine III to provide a C-13 esterified 1,14 carbonate 7-hydroxy 14β-hydroxy-10-acetylbaccatine III; and*

*g. removing a dimethoxybenzylidene group from the C-13 esterified 1,14 carbonate 7-hydroxy 14β-hydroxy-10-acetylbaccatine III to provide 13-(N-Boc-β-isobutylisoserinyl)-14β-hydroxy-baccatine III 1,14-carbonate.*

*11. The process of claim 10, wherein the silylating agent is triethyl chlorosilane.*

*12. The process of claim 10, wherein the 7-triethylsilyl 14β-hydroxy-10-deacetylbaccatine III is reacted with phosgene by dissolving the 7-triethylsilyl 14β-hydroxy-10-deacetylbaccatine III in a methylene chloride/pyridine mixture in a 3:1 ratio and then adding a toluene solution containing phosgene to the methylene chloride/pyridine mixture under a nitrogen atmosphere.*

*13. The process of claim 10, wherein the 1,14 carbonate 7-triethylsilyl 14β-hydroxy-10-deacetylbaccatine III is reacted with LiHMDS in anhydrous THF.*

*14. The process of claim 10, wherein the lithium salt of the 10-hydroxyl group of the 1,14 carbonate 7-triethylsilyl 14β-hydroxy-10-deacetylbaccatine III is acetylated with acetyl chloride.*

*15. The process of claim 10, wherein the 1,14 carbonate 7-triethylsilyl 14β-hydroxy-10-acetylbaccatine III is reacted with the (4S, 5R)-N-Boc-2-(2,4-dimethoxyphenyl)-4-isobutyl-1-oxazolidine-5-carboxylic acid in an anhydrous apolar organic solvent in the presence of a base and of a condensing agent.*

*16. The process of claim 15, wherein the condensing agent is dicyclohexylcarbodiimide.*

*17. The process of claim 10, wherein the 7-triethylsilyl group is removed from the C-13 esterified 1,14 carbonate 7-triethylsilyl 14β-hydroxy-10-acetylbaccatine III with pyridinium fluoride in an acetonitrile/pyridine solution under nitrogen, and the dimethoxybenzylidene group is removed from the C-13 esterified 1,14 carbonate 7-hydroxy 14β-hydroxy-10-acetylbaccatine III in a methylene chloride solvent by addition of methanolic HCl followed by addition of* $NaHCO_3$.

*18. The process of claim 10, wherein the (4S, 5R)-N-Boc-2-(2,4-dimethoxyphenyl)-4-isobutyl-1-oxazolidine-5-carboxylic acid is prepared by the process comprising the steps of:*

*a. protecting the amino group of a leucinol with Boc to form N-Boc-L-leucinol;*

*b. converting the N-Boc-L-leucinol into N-Boc-L-leucinal;*

*c. preparing a cyanhydrin nitrile from the N-Boc-L-leucinal;*

*d. transforming the cyanhydrin nitrile into a carboxylic acid;*

*e. forming a methyl ester of the carboxylic acid;*

*f. purifying the methyl ester of the carboxylic acid;*

*g. condensing the product of step (f) with 2,4-dimethoxybenzaldehyde dimethyl acetal to form (4S, 5R)-N-Boc-2-(2,4-dimethoxyphenyl) 4-isobutyl-1-oxazolidine-5-carboxylic acid methyl ester; and*

*h. transforming the (4S, 5R)-N-Boc-2-(2,4-dimethoxyphenyl)-4-isobutyl-1-oxazolidine-5-carboxylic acid methyl ester into the (4S, 5R)-N-Boc-2-(2,4-dimethoxyphenyl)-4-isobutyl-1-oxazolidine-5-carboxylic acid.*

*19. The process of claim 2, wherein the 13-(N-Boc-β-isobutylisoserinyl)-14β-hydroxy-baccatine III 1,14-carbonate is prepared by a process comprising the steps of:*

*a. acetylating the C-10 hydroxyl of 14β-hydroxy-10-deacetylbaccatine III to provide 14β-hydroxy-10-acetylbaccatine III:*

*b. reacting 14β-hydroxy-10-acetylbaccatine III with phosgene to provide a 1,14 carbonate derivative of 14β-hydroxy-10-acetylbaccatine III;*

*c. silylating the C-7 hydroxyl of the 1,14 carbonate derivative of 14β-hydroxy-10-acetylbaccatine III to provide a 7-silyl 1,14 carbonate derivative of 14β-hydroxy-10-acetylbaccatine III;*

*d. reacting the 7-silyl 1,14 carbonate derivative of 14β-hydroxy-10-acetylbaccatine III with (4S,5R)-N-Boc-2-(2,4-dimethoxyphenyl)-4-isobutyl-1-oxazolidine-5-carboxylic acid to provide a C-13 esterified 7-silyl 1,14 carbonate derivative of 14β-hydroxy-10-acetylbaccatine III;*

*e. removing the 7-silyl group from the C-13 esterified 7-silyl 1,14 carbonate derivative of 14β-hydroxy-10-acetylbaccatine III to provide a C-13 esterified 7-hydroxy 1,14 carbonate derivative of 14β-hydroxy-10-acetylbaccatine III; and*

*f. removing a dimethoxybenzylidene group from the C-13 esterified 7-hydroxy 1,14 carbonate derivative of 14β-hydroxy-10-acetylbaccatine III to provide 13-(N-Boc-β-isobutylisoserinyl)-14β-hydroxy-baccatine III 1,14-carbonate.*

*20. The process of claim 19, wherein the C-10 hydroxyl of 14β-hydroxy-10-deactylbaccatine III is acetylated with acetic anhydride in the presence of a cerium, scandium, or ytterbium salt.*

*21. The process of claim 20, wherein the salt is* $CeCl_3.H_2O$.

*22. The process of claim 19, wherein 14β-hydroxy-10-acetylbaccatine III is reacted with phosgene by dissolving the 14β-hydroxy-10-acetylbaccatine III in a methylene chloride/pyridine mixture in a 3:1 ratio and then adding a toluene solution containing phosgene to the methylene chloride/pyridine mixture under a nitrogen atmosphere.*

*23. The process of claim 19, wherein the C-10 hydroxyl of 14β-hydroxy-10-deacetylbaccatine III is acetylated with acetyl chloride.*

*24. The process of claim 19, wherein the 7-silyl 1,14 carbonate derivative of 14β-hydroxy-10-acetylbaccatine III is reacted with (4S, 5R)-N-Boc-2-(2,4-dimethoxyphenyl)-4-isobutyl-1-oxazolidine-5-carboxylic acid in an anhydrous apolar organic solvent in the presence of a base and a condensing agent.*

*25. The process of claim 24, wherein the condensing agent is dicyclohexylcarbodiimide.*

*26. The process of claim 19, wherein the silyl protective group is removed from the C-13 esterified 7-silyl 1,14 carbonate derivative of 14β-hydroxy-10-acetylbaccatine III with pyridinium fluoride in a acetonitrile/pyridine solution under nitrogen, and the dimethoxybenzylidene group is removed from the C-13 esterified 7-hydroxy 1,14 carbonate*

*derivative of 14β-hydroxy-10-acetylbaccatine III in a methylene chloride solvent by addition of methanolic HCl followed by addition of $NaHCO_3$.*

*27. The process of claim 19, wherein the (4S,5R)-N-Boc-2-(2,4-dimethoxyphenyl)-4-isobutyl-1-oxazolidine-5-carboxylic acid is prepared by the process comprising the steps of:*

*a. protecting the amino group of a leucinol with Boc to form N-Boc-L-leucinol;*

*b. converting the N-Boc-L-leucinol into N-Boc-L-leucinal;*

*c. preparing a cyanhydrin nitrile from the N-Boc-L-leucinal;*

*d. transforming the cyanhydrin nitrile into a carboxylic acid;*

*e. forming a methyl ester of the carboxylic acid;*

*f. purifying the methyl ester of the carboxylic acid;*

*g. condensing the product of step (f) with 2,4-dimethoxybenzaldehyde dimethyl acetal to form (4S, 5R)-N-Boc-2-(2,4-dimethoxyphenyl) 4-isobutyl-1-oxazolidine-5-carboxylic acid methyl ester; and*

*h. transforming the (4S, 5R)-N-Boc-2-(2,4-dimethoxyphenyl)-4-isobutyl-1-oxazolidine-5-carboxylic acid methyl ester into the (4S, 5R)-N-Boc-2-(2,4-dimethoxyphenyl)-4-isobutyl-1-oxazolidine-5-carboxylic acid.*

*28. The process of claim 2, wherein the 13-(N-Boc-β-isobutylisoserinyl)-14β-hydroxy-baccatine III 1,14-carbonate is prepared by a process comprising the steps of:*

*a. transforming 14β-hydroxy-10-deacetylbaccatine III into a triethylsilylated derivative at the 7-position;*

*b. preparing a 1,14 carbonate derivative from the product of step (a);*

*c. selectively acetylating the 10-hydroxyl;*

*d. reacting the product of step (c) with (4S, 5R)-N-Boc-2-(2,4-dimethoxyphenyl)-4-isobutyl-1-oxazolidine-5-carboxylic acid;*

*e. cleaving the triethylsilyl and dimethoxybenzylidene protective groups from the product of step (d).*

*29. The process of claim 28, wherein the silylating agent of step (a) is triethyl chlorosilane; the 1,14 carbonate derivative in step (b) is prepared using phosgene in toluene in a 3:1 methylene chloride/pyridine solution under nitrogen atmosphere; step (c) is carried out with LiHMDS in anhydrous THF, and the resulting 10-hydroxy derivative is subsequently acetylated with acetyle chloride; step (d) is carried out in anhydrous apolar organic solvent, in the presence of a base and the condensing agent dicyclohexylcarbodiimide (DCC); the triethylsilyl protective group in step (e) is removed with pyridinium fluoride in acetonitrile/pyridine solution under nitrogen, and the dimethoxybenzylidene protective group is removed in methylene chloride solvent by addition of HCl in methanol and subsequently addition of $NaHCO_3$.*

*30. The process of claim 28, wherein the (4S,5R)-N-Boc-2-(2,4-dimethoxyphenyl)-4-isobutyl-1-oxazolidine-5-carboxylic acid is prepared by the process comprising the steps of:*

*a. protecting the amino group of a leucinol with Boc to form N-Boc-L-leucinol;*

*b. converting the N-Boc-L-leucinol into N-Boc-L-leucinal;*

*c. preparing a cyanhydrin nitrile from the N-Boc-L-leucinal;*

*d. transforming the cyanhydrin nitrile into a carboxylic acid;*

*e. forming a methyl ester of the carboxylic acid;*

*f. purifying the methyl ester of the carboxylic acid;*

*g. condensing the product of step (f) with 2,4-dimethoxybenzaldehyde dimethyl acetal to form (4S, 5R)-N-Boc-2-(2,4-dimethoxyphenyl) 4-isobutyl-1-oxazolidine-5-carboxylic acid methyl ester; and*

*h. transforming the (4S, 5R)-N-Boc-2-(2,4-dimethoxyphenyl)-4-isobutyl-1-oxazolidine-5-carboxylic acid methyl ester into the (4S, 5R)-N-Boc-2-(2,4-dimethoxyphenyl)-4-isobutyl-1-oxazolidine-5-carboxylic acid.*

*31. The process of claim 2, wherein the 13-(N-Boc-β-isobutylisoserinyl)-14β-hydroxy-baccatine III 1,14-carbonate is prepared by a process comprising the steps of:*

*a. selectively acetylating the hydroxyl at the C-10 of 14β-hydroxy-10-deacetylbaccatine III;*

*b. preparing a 1,14 carbonate derivative from the product of step (a);*

*c. silylating the hydroxyl at C-7;*

*d. reacting the product of step (c) with (4S, 5R)-N-Boc-2-(2,4-dimethoxyphenyl)-4-isobutyl-1-oxazolidine-5-carboxylic acid;*

*e. cleaving the triethylsilyl and dimethoxybenzylidene protective groups from the product of step (d).*

*32. The process of claim 31, wherein step (a) is carried out with acetic anhydride in the presence of a cerium, scandium or ytterbium salt, the 1,14 carbonate derivative in step (b) is prepared using phosgene in toluene in a 3:1 methylene chloride/pyridine solution under nitrogen atmosphere; step (c) is carried out with LiHMDS in anhydrous THF, and the resulting 10-hydroxy derivative is subsequently acetylated with acetyle chloride; step (d) is carried out in anhydrous apolar organic solvent, in the presence of a base and the condensing agent dicyclohexylcarbodiimide (DCC); the triethylsilyl protective group in step (e) is removed with pyridinium fluoride in acetonitrile/pyridine solution under nitrogen, and the dimethoxybenzylidene protective group is removed in methylene chloride solvent by addition of HCl in methanol and subsequently addition of $NaHCO_3$.*

*33. The process of claim 32, wherein the cerium salt comprises $CeCl_3 7H_2O$.*

*34. The process of claim 31, wherein the (4S,5R)-N-Boc-2-(2,4-dimethoxyphenyl)-4-isobutyl-1-oxazolidine-5-carboxylic acid is prepared by the process comprising the steps of:*

*a. protecting the amino group of a leucinol with Boc to form N-Boc-L-leucinol;*

*b. converting the N-Boc-L-leucinol into N-Boc-L-leucinal;*

*c. preparing a cyanhydrin nitrile from the N-Boc-L-leucinal;*

*d. transforming the cyanhydrin nitrile into a carboxylic acid;*

*e. forming a methyl ester of the carboxylic acid;*

*f. purifying the methyl ester of the carboxylic acid;*

*g. condensing the product of step (f) with 2,4-dimethoxybenzaldehyde dimethyl acetal to form (4S, 5R)-N-Boc-2-(2,4-dimethoxyphenyl) 4-isobutyl-1-oxazolidine-5-carboxylic acid methyl ester; and*

*h. transforming the (4S,5R)-N-Boc-2-(2,4-dimethoxyphenyl)-4-isobutyl-1-oxazolidine-5-carboxylic acid methyl ester into the (4S, 5R)-N-Boc-2-(2,4-dimethoxyphenyl)-4-isobutyl-1-oxazolidine-5-carboxylic acid.*

* * * * *